United States Patent [19]

Morris et al.

[11] Patent Number: 4,714,874
[45] Date of Patent: Dec. 22, 1987

[54] TEST STRIP IDENTIFICATION AND INSTRUMENT CALIBRATION

[75] Inventors: James R. Morris, South Bend; James A. White, Elkhart, both of Ind.

[73] Assignee: Miles Inc., Elkhart, Ind.

[21] Appl. No.: 797,214

[22] Filed: Nov. 12, 1985

[51] Int. Cl.⁴ .................... G01R 27/02; G01N 21/78
[52] U.S. Cl. .................. 324/65 R; 422/58; 324/444
[58] Field of Search ............ 340/686, 870.38; 324/65 R, 158 R, 444, 446, 449, 158 F; 29/574; 148/DIG. 102; 422/58, 57, 104; 338/334

[56] References Cited
U.S. PATENT DOCUMENTS

| 2,785,057 | 3/1957 | Schwab et al. | 422/58 |
| 3,808,527 | 4/1974 | Thomas | 324/65 R |
| 4,344,064 | 8/1982 | Bitler et al. | 338/334 |
| 4,382,063 | 5/1983 | Romito et al. | 422/58 X |
| 4,538,105 | 8/1985 | Ausschnitt | 324/65 R X |
| 4,618,475 | 10/1986 | Wang | 422/58 X |

Primary Examiner—Reinhard J. Eisenzopf
Assistant Examiner—Jack B. Harvey
Attorney, Agent, or Firm—Roger N. Coe

[57] ABSTRACT

Test device apparatus is disclosed containing a electrically conductive region which provides information concerning the nature of the test device and/or its position. In a preferred embodiment a conductive strip is applied to a test device and used to determine the identification of the test device, the position of the test device and/or calibrate an instrument which is used to read the test device. The conductive strip generates a signal by measuring the resistance ratio of the electrical path through its conductive region using three or more electrodes or probes. The signal obtained by the electrodes is used to determine the characteristics indicated above or to program operational parameters within an instrument used to analyze the test device.

2 Claims, 7 Drawing Figures

TEST STRIP IDENTIFICATION AND INSTRUMENT CALIBRATION

FIELD OF THE INVENTION

The present invention relates to apparatus and a process for identifying test devices and calibrating instrumentation used in connection with such test devices and, more particularly, the invention relates to the application of a conductive path or region to a test device for use in the identification of the test device and/or calibration of instrumentation employed in conjunction with the test device.

BACKGROUND OF THE INVENTION

Increasingly, test devices in the form of reagent strips are being used to provide convenient and rapid analysis of various types of samples, including liquid samples of biological, industrial and other fluid substances. Diagnostic test devices designed for detecting various clinically significant substances or constituents in body fluids, such as urine and blood, have in many cases supplanted prior wet chemistry techniques which were both cumbersome and time consuming. Diagnostic test devices have assisted in the fast, inexpensive and accurate diagnosis and treatment of disease.

Conventional test devices generally comprise an absorbent or porous matrix incorporated with indicator reagents which produce a detectable result, usually of a colorimetric nature. The sample to be tested is contacted with the matrix, such as by momentary immersion, where the sample is liquid, and an indicator response is observed after a period of time. The response can be observed instrumentally or visually, depending on the particular test device. In the detection of occult blood in urine, for example, a diagnostic test device can be employed which comprises absorbent paper as the matrix impregnated with o-tolidine and peroxide. When this test device is wetted with urine containing occult blood, decomposition of the peroxide occurs with the accompanying oxidation of the o-tolidine to provide a color response. This test is sensitive and extremely useful in diagnosing urinary tract disorders.

For ease in handling, the absorbent or porous matrix, sometimes called a "carrier matrix", is advantageously affixed to one end of an insoluble support member such as an organoplastic strip, e.g., polystyrene, by suitable means such as double faced adhesive tape. Optically transparent substrate material known as Trycite, polystyrene film obtained from Dow Chemical Company, is preferred. The support member normally has a thickness of about 0.19 mm, a width of about 5 mm and a length which can vary depending on the intended use, the number of reagent carrier matrices present, etc. Currently, test devices are being made by the Ames Division of Miles Laboratories, Inc. having lengths of about 85.5 mm and about 82.5 mm. Obviously, based on these dimensions and the materials involved, such test devices tend to be small, elongated and flexible in nature.

Notwithstanding the use of "identical" materials and reagents for the manufacture of test devices, variations occur from one batch to the next and such variations can be significant enough to affect the performance characteristics of a particular test device. Accordingly, test manufacturers have found that it is normally necessary to calibrate instrumentation used in connection with such test devices in order to compensate for variations from lot to lot in the test devices manufactured. In addition, manufacturers have found that it is desirable to code test devices which are to be read by instrumentation with some kind of identification in order to make certain that the test device used for a particular analysis correctly correlates with the instrumentation used to measure or read the test device.

Manufacturers have also sought means for assuring users of test devices that a test device inserted into automated equipment is properly aligned and accurately positioned with respect to the automatic readout means. Misalignment, or misregistration, can result in an improper identification or reading of the test device.

Various techniques have been suggested for encoding information into or on a strip, including application of a magnetizable film (EP No. 132 790 A), the perforation of a strip (U.S. Pat. No. 3,526,480) with a coded pattern, the application of different fluorogens which can be scanned by a fluorescent scanning device (U.S. Pat. No. 3,551,295), and the application of an optical type bar coding (U.S. Pat. No. 4,510,383) for imparting information which can be transmitted to instrumentation.

Optical readers tend to be expensive. Moreover, light radiating means and light sensitive receivers tend to be sensitive to variations in positioning of a test device. The application of a magnetic strip to test devices, on the other hand, has the disadvantage that the magnetic pattern must be scanned to provide useful information, i.e., the coding element must move relative to the reading element; the magnetic pattern is subject to being erased and/or altered due to nearby electrical or magnetic fields such as those from motors, etc.; and the coding of information into a magnetic field and the retrieval of the coded information requires relatively sophisticated and expensive equipment.

In U.S. Pat. No. 3,000,498 graphite based ink is applied to the rear surface of a postal stamp in portions where the stamp is strongly colored or heavily printed. The printing is invisible to the naked eye but detectable by sensors moving across the stamp to determine the value of the stamp.

In U.S. Pat. No. 4,230,938 electrosensitive material is applied to checks, business forms and the like in the form of bar codes of horizontal synchronization marks or vertical synchronization marks or timing tracks which can be sensed by moving a sensor over the forms.

The present invention has been developed for the purpose of providing an improved system for the identification of test devices as well as the calibration of instrumentation used with such test devices. In addition, the system which has been developed can be used for the purpose of assuring proper alignment between a test device and instrumentation.

SUMMARY OF THE INVENTION

An object of the present invention is to provide a test device containing improved identification means.

Another object of the present invention is to provide a test device containing improved means for calibration of instrumentation.

Yet another object of the present invention is to provide means for use in confirming proper alignment between a test device and instrumentation.

Still another object of the present invention is to provide a method of manufacturing test devices with means for identifying and/or aligning the test device and/or calibrating instrumentation.

In accordance with the present invention, at least one conductive path is applied to a test device. Upon contact of the conductive material with probes a ratio measurement is obtained based on resistivity, conductivity or capacitance which is used to identify the nature of the test device and/or determine its alignment. Information on the nature of the test device imparted by the ratio measurement can include information as to the type of test device, as well as information which will permit calibration of instrumentation to select optimum system operation parameters for analysis of the test device. Methods for the manufacture of such a test device and the use of the test device are also disclosed.

DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE PREFERRED EMBODIMENTS

Figure 1:
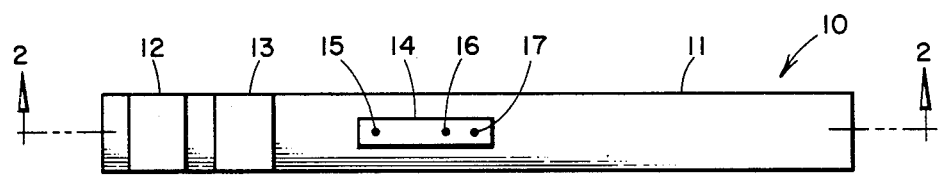
FIG. 1 is a top schematic view of a test device showing two reagent matrices and a conductive strip applied to a substrate.
Figure 2:
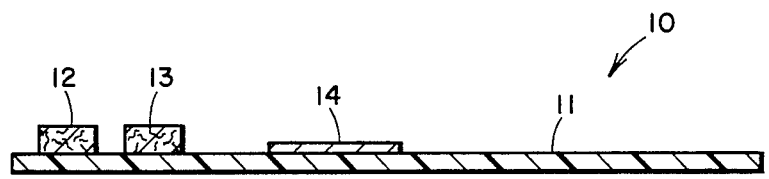
FIG. 2 is a cross-sectional view taken along lines 2—2 of the test device illustrated in FIG. 1.

Referring to FIGS. 1 and 2, test device 10 is illustrated comprising multiple reagent matrices 12 and 13 attached to substrate 11. A conductive strip 14 is also applied to substrate 11 on the same surface as reagent matrices 12 and 13. By contacting this conductive strip with at least three electrodes or probes (not shown) the signal generated is proportional to the resistance of the electrical path through the conductive region of conductive strip 14 between the probes and the resulting signals can be ratioed to correlate certain operational parameters, e.g., algorithms, wavelengths, etc., of an instrument used to "read" or measure test device 10. Probes can contact conductive strip 14 at suitable contact points such as contact points 15, 16 and 17 to obtain a ratio of the resistance between contact points 15 and 16 and between points 16 and 17 or another suitable ratio such as the ratio of the resistance between points 15 and 17 and points 15 and 16 or points 16 and 17. Provided contact points 15, 16 and 17 are not equidistant from each other a ratio of resistance values can be obtained. If one or more of the probes fails to contact conductive strip 14 there is an immediate indication of misalignment of test device 10 in the instrumentation. Secondly, conductive strip 14 can be correlated for purposes of identifying the particular test device and automating or indexing instrumentation used to obtain test results. This is of particular importance when the same instrument is being used to make determinations under different operating parameters with respect to different test devices, all of which have an overall configuration of approximately the same dimensions. Thus, currently, it is conventional practice to incorporate 1 to 8 or more reagent matrices on the same size substrate. An instrument must be programmed manually or automatically to determine the number, kind and location of the carrier matrices on each test device in order that appropriate operational parameters are applied in conjunction with the reaction which occurs in each of the carrier matrices of the test device. The present invention provides the means for instructing instrumentation as to which system operation parameters to apply in the analysis of the tests associated with test device 10.

It will be understood that two carrier matrices on test device 10 have been shown only for purposes of illustration. Obviously, one or more carrier matrices can be present and, as indicated above, the conductive strip 14 can be used to identify the number and type of carrier matrices present on a particular test device.

Conductive strip 14 can be made of any suitable conductive material such as silver, gold, nickel, metal alloys, etc., applied in the form of metal filled polymer, metal powder, etc. The conductive path can be applied to the reagent test device using any convenient technique, including application to a substrate as a tape, as a paint (applied with a brush or a spray), as an ink (applied using type font or spray), or otherwise incorporated into or onto the test devices during or following the manufacturing operation. Thus, the conductive material can be applied as a thin layer of film by incorporating metal in a polymeric substance (e.g., epoxy) which will adhere to substrate 11. Tape can be adhesively bound to substrate 11. Conductive strip 14 can also be applied using sputtering, low pressure heat vaporization or electroplating techniques so as to apply conductive material to the surface of substrate 11.

A preferred type of conductive element is the cermet chip resistor which is available from CAL-R Inc. of Santa Monica, Calif. Resistance ranges can be formulated ranging from 10 ohms to 40 megaohms in a chip having a thickness ranging from 0.03 to 0.07 cm. Gold epoxy paste, gold filled conductive bonding preparations exhibiting high electrical conductivity and bond strength, are available from Transene Company, Inc., of Rowley, Mass. under the trademarks Gold Epoxy GE10, GE20, GE30 and GE40. These pastes have electrical resistivity of $4 \times 10^{-4}$, $7 \times 10^{-4}$, $7 \times 10^{-4}$ and $6 \times 10^{-4}$ ohms cm, respectively. In addition, from the same company, silver bond conductive adhesives are available under the designations Type 40, Type 50 and Type 60 having an electrical resistivity of $1 \times 10^{-4}$ ohms cm. The silver bond is a two component epoxy based conductive adhesive of silver filled epoxy having a consistency of a soft thixotropic paste. The Transene Company also makes a Nickel-Met preparation which is the form of a paint or paste containing nickel powder and an acrylate base. Butyl acetate is used as a solvent in the paint formulation whereas butyl carbitol acetate is used as a solvent in the paste composition. The resistivity of the paint composition is $3.4 \times 10^{-3}$ ohms cm and the resistivity of the paste is $6.0 \times 10^{-3}$ ohms cm. The paint composition can be applied by spraying or painting following by air cure to a nominal thickness of 1-2 mils. The paste can be screen printed and dried at 100° C.

It will be understood that while conductive path 14 has been illustrated as being applied to the same surface of substrate 11 as reagent matrices 12 and 13 theoretically, at least, there is no reason why conductive path 14 could not be applied to the opposite surface of substrate 11 or even applied to the one of the edges of substrate 11.

In FIGS. 1 and 2 conductive path 14 is shown in an elongated rectangular configuration. It will be understood that this particular configuration is a convenient one but that other configurations can be employed including those illustrated in FIGS. 3 and 4 as well as serpentine or other more complex configurations or shapes. A "V" shape configuration is easy to apply and useful in aligning a test device. Conductive networks or paths with more than one conductance path of resistance can also be applied.

The size of the conductive path 14 needs to be sufficient to easily facilitate contact with electrodes or probes for purpose of determining a ratio of resistance in the conductive path and thus the size of conductive path 14 can actually be determined by the type of material used, convenience in making the measurements and the location of the conductive path on a test device.

Figure 3:
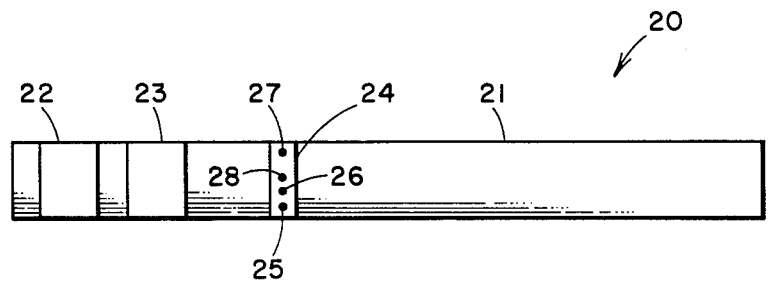
FIG. 3 is a schematic top view of another test device in accordance with the present invention illustrating reagent matrices and a conductive strip applied to a substrate.

The test device 20 illustrated in FIG. 3 is similar to that of test device 10 illustrated in FIGS. 1 and 2. Reagent matrices 22 and 23 correspond to reagent matrices 12 and 13, respectively. FIG. 3, however, illustrates a conductive path 24 which extends at right angles across the substrate 21 rather than lengthwise, as in FIG. 1. In FIG. 3 a resistance ratio is obtained from the resistance value between contact points 25 and 26, and the resistance value between contact points 27 and 28.

Figure 4:
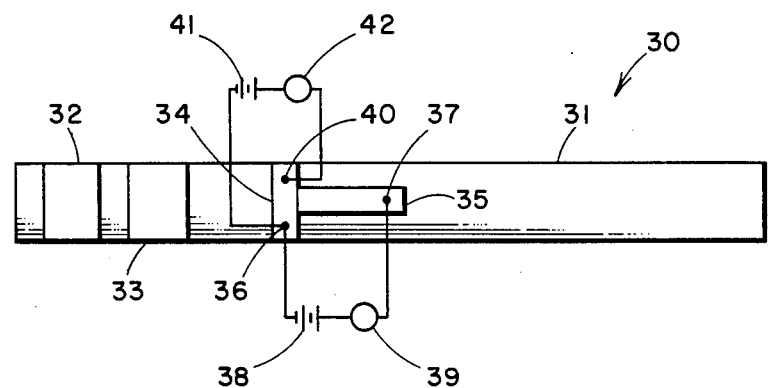
FIG. 4 is yet another embodiment of the present invention illustrating schematically the top view of a test device having reagent matrices and a "T-shaped" conductive path applied to a substrate, the conductive path capable of being contacted at three or more points for determination of the resistance in the electrical path between the points.

In FIG. 4 test device 30 is illustrated with reagent matrices 32 and 33 attached to substrate 31 and a "T-shaped" conductive path formed by conductive members 34 and 35. Conductive members 34 and 35 can, if desired, be made from the same or different conductive materials. FIG. 4 illustrates an electrical connection being made from probe contact points 36 and 37 through power source 38 and meter 39. This permits a first conductive measurement to be made. A second electrical connection is shown being made from probe contact points 36 and 40 through power source 41 and meter 42. This permits a second conductive measurement to be made which is then ratioed with the first conductive measurement. The embodiment of FIG. 4 is particularly useful in assuring proper alignment between the test device and instrumentation employed for measurement of a test device since probes must contact points 36, 37 and 40 in order for any ratio signal to be generated.

Figure 5:
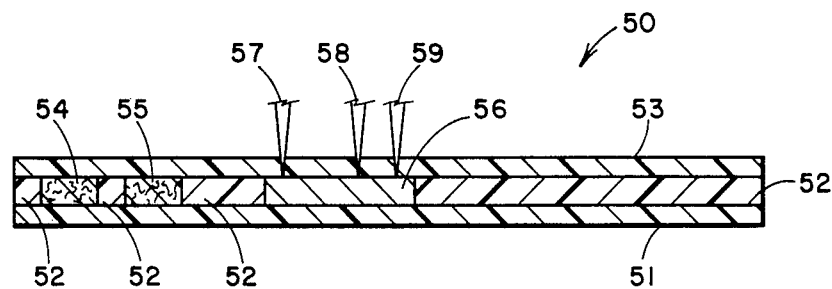
FIG. 5 is a schematic side view in cross section of a multilayered test device showing probes penetrating a coating layer to contact conductive material present beneath the coating layer.

Still another embodiment of the invention is illustrated in FIG. 5 by test device 50. This test device comprises a multilayered member having a substrate 51 and an intermediate layer 52. Conductive material 56 and reagent matrices 54 and 55 are present in intermediate layer 52. A top or overcoat protective layer 53 is applied to intermediate layer 52. It is necessary for probes 57, 58 and 59 to physically penetrate the overcoat or top layer 53 in the manner shown and contact conductive material 56 thereby permitting resistance ratio measurements to be made.

It will be understood that other configurations of multilayered devices are possible and that FIG. 5 illustrates only one particular embodiment.

Figure 6:
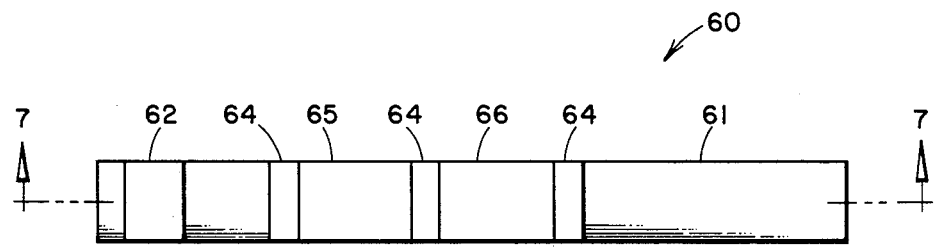
FIG. 6 is a top schematic view of a test device having multiple conductive paths for measuring resistance ratios.
Figure 7:
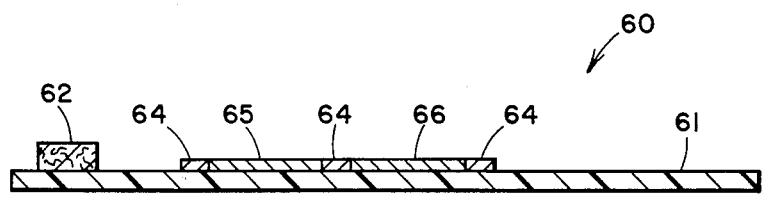
FIG. 7 is a cross-sectional view taken along lines 7—7 in FIG. 6.

Another approach is illustrated in FIGS. 6 and 7 for measuring resistance ratios. These figures illustrate a reagent test device 60 comprising reagent matrix 62 attached to substrate 61. Also present on substrate 61 are conductive areas 64 which are separated by resistance materials 65 and 66. By using two probes to contact the metal conductor portions 64 on either side of resistance element 65 and the metal conductor portions 64 on either side of resistance element 66 a ratio of resistances can be obtained which is then used to convey information pertaining to the identification, positioning, nature of the test device or calibration. Alternatively, three probes can be utilized to simultaneously contact metal conductive portions 64 of test device 60 and thereby obtain a ratio of resistance values. Thus the absolute value of resistance is not important but only the ratio of resistances. Normally the resistance values of resistance materials 65 and 66 will be quite different such that a distinct ratio of the two resistance values will be obtained. While it is not necessary to limit the ratio to a ratio of two values, normally only two resistance materials are required and additional resistance materials only add to the expense and complicate manufacturing procedures.

Metal conductor areas 64 can be formed from any suitable conductive material and applied to substrate 61 in any suitable fashion. Similarly, resistance elements 65 and 66 can be formed from any suitable resistance materials and applied in any suitable fashion to substrate 61. The conductive and resistive areas must be contiguous (i.e., in electrical contact) so that it is possible to obtain a conductance value by contacting metal conductors 64 with probes.

In a preferred embodiment the conductive and resistive materials are applied to substrate 61 using thick film techniques for depositing various mixtures of conductive materials and resistive materials to the substrate. Such techniques normally involve applying the materials by a printing or silk screening process. However, a paste mixture can be applied by doctor blade to substrate 61. Among the thick film screen printable resistor pastes are those of Thick Film Systems of Santa Barbara, California, designated by the name Powerohm 850 series, which are resistive formulations of screen printable paste for thick film applications normally applied in microcircuits or for discrete components which require high reliability and close control of properties. The resistance values for such materials can vary over a wide range, varying from a few hundred ohms to several hundred thousand ohms. The actual value of resistance is not important as long as it can be measured. Of course, in the case of the embodiment illustrated in FIGS. 6 and 7 there is a difference between the resistance values of elements 65 and 66.

The invention solves several problems associated with the use of test devices. First of all, the calibration strip can be used to identify a particular test device and "program" instrumentation to "read" that particular test device. Secondly, the calibration strip can be used to indicate the correct placement or positioning of a test device in an instrument. One recurrent problem with reagent strip measurement lies in the improper positioning of the reactive areas of the test device in the optical path of an instrument. Despite the presence of mechanical guides and optical signals used to help detect errors in positioning, such errors still occur. The conductive path can be used to replace other error detection means or supplement other means used to test for proper positioning. As indicated above, the "T-shaped" configuration illustrated in FIG. 4 is one configuration which requires a positive signal as an indication that strip positioning along two axes is correct. Obviously, more complicated networks of conductance can be used for checking the position of a test device.

Finally, the conductive strip of the present invention permits system calibration to occur. Signals from a conductive region can be used to select or program calibration parameters specific for an assay on a test device. Based on the ratio of resistance values obtained, the wavelength and/or time period for making a reading and/or mathematical evaluation applied to a reading can be selected automatically by a measuring instrument. Other methods of system calibration such as live calibration, and the like, are subject to user errors. While such methods are fundamental to preparing a system for use, they are peripheral to the primary task of sample application and measurement. Consequently, errors that occur during calibration can significantly limit system performance. At a minimum the necessity of such calibration reduces operator convenience. The use of a conductive path on the test device which is used to obtain a ratio measurement directly by the instrument and which is used in calibrating the instrument requires very little user involvement and is less prone to user variability or error during the calibration procedure. No movement of the sensors or probes relative to the reagent strip is required. System convenience is increased because fewer operating techniques must be learned and the familiar methods of sample application and reagent strip measurement are not altered.

From the foregoing, it will be seen that this invention is well adapted to attain all of the ends and objects hereinabove set forth, together with other advantages which obvious and which are inherent to the system. The described system requires only static contact between three or more probes and one or more conductive strips. There is no encoding and decoding of data bits from a surface. The conductive strip is not altered by exposure to electrical or magnetic devices and the conductive strip is not a field effect device in which information must be coded entirely within the device. The conductive strip can be easily attached on or incorporated in a test device at low cost. Existing technology concerning manufacture of test devices does not have to be altered in order to include conductive paths in accordance with the present invention. The ratioing of resistance values (or conductance values) also tends to compensate for correlated errors and avoids many of the problems associated with attempting to obtain an absolute resistance value.

Obviously, many other modifications and variations of the invention as hereinbefore set forth can be made without departing from the spirit and scope of the invention.

What is claimed is:

1. A method for identifying a reagent test device having an electrically conductive region and calibrating a reagent test device measuring instrument for the identified reagent test device comprising
   contacting a conductive region of a reagent test device in a first location with electrical probes to make a first resistance or conductance measurement signal,
   contacting the same or a different conductive region of said reagent test device in a second location with electrical probes to make a second resistance or conductance measurement signal,
   ratioing the first and second measurement signals, and
   transmitting the ratioed signals to an instrument, thereby identifying the reagent test device and calibrating said instrument.

2. The method of claim 1 in which one conductive region having uniform conductance is present and the two measurement signals are obtained by contacting the conductive region at nonequidistant contact points with three electrical probes and then apply a current through two probes at a time to obtain said first and second measurement signals.

* * * * *